United States Patent [19]
Albino et al.

[11] Patent Number: 4,806,628
[45] Date of Patent: Feb. 21, 1989

[54] MONOCLONAL ANTIBODIES AGAINST MELANOCYTES

[75] Inventors: Anthony Albino, New York, N.Y.; J. Gregory Cairncross, London, Canada; Magdalena Eisinger, Demarest, N.J.; Alan N. Houghton; Lloyd Old, both of New York, N.Y.

[73] Assignee: Sloan-Kettering Institute for Cancer Research, New York, N.Y.

[21] Appl. No.: 840,632

[22] Filed: Mar. 17, 1986

Related U.S. Application Data

[63] Continuation of Ser. No. 445,561, Nov. 30, 1982, abandoned.

[51] Int. Cl.$^4$ .......................... C07K 15/00; C12N 5/00
[52] U.S. Cl. .................................. 530/387; 530/808; 530/809; 435/68; 435/172.2; 435/240.26; 435/7; 424/85.8; 935/89; 935/95; 935/106; 436/548

[58] Field of Search ....................... 530/387, 808, 809; 424/85; 435/68, 172.2, 240; 935/89, 95, 106; 436/548

[56] References Cited

U.S. PATENT DOCUMENTS 4,562,160 12/1985 Real et al. ............................ 530/387
4,650,756 3/1987 Old et al. .......................... 435/172.2

Primary Examiner—Delbert R. Phillips
Assistant Examiner—Garnette D. Draper
Attorney, Agent, or Firm—John P. White

[57] ABSTRACT

Monoclonal antibodies were discovered which recognize differentiation antigens on melanocytes and melanoma cells at various stages of differentiation. A system of classification based on these antigens is proposed and their use in the diagnosis and treatment of melanoma is given.

3 Claims, No Drawings

MONOCLONAL ANTIBODIES AGAINST MELANOCYTES

This is a continuation of application Ser. No. 445,561, filed Nov. 30, 1982, now abandoned.

This invention concerns monoclonal antibodies against melanocytes and melanomas. The monoclonal antibodies recognize antigenic markers on and in melanocytes and melanomas and are useful in classifying melanoma cells according to stage of differentiation. Immunoassays for melanocytes and melanoma cells based on these markers are presented.

INTRODUCTION

The introduction by Köhler and Millstein in 1975 of a revolutionary new procedure for the routine production of monoclonal antibodies using hybridomas allows the production of almost unlimited quantities of antibodies of precise and reproducible specificity. While conventional antisera produced by immunizing animals with tumor cells or other antigens contain a myriad of different antibodies differing in their specificity and properties, hybridomas produce a single antibody with uniform characteristics. The Kohler-Millstein procedure entails the fusion of spleen cells from an immunized animal with an immortal myeloma cell line. From the fused cells (hybridomas), clones are selected that produce antibody of the desired specificity. As hybridoma cells can be cultured indefinitely (or stored frozen in liquid nitrogen), a constant supply of antibody is assured.

Antibodies are proteins that have the ability to combine with and recognize other molecules, known as antigens. Monoclonal antibodies are no different from other antibodies except that they are very uniform in their properties and recognize only one antigen or a portion of an antigen known as a determinant.

In the case of cells, the determinant recognized is an antigen on or in the cell which reacts with the antibody. It is through these cell antigens that a particular antibody recognizes, i.e. reacts with, a particular kind of cell. Thus the cell antigens are markers by which the cell is identified.

These antigenic markers may be used to observe the normal process of cell differentiation and to locate abnormalities within a given cell system. The process of differentiation is accompanied by changes in the surface antigenic phenotype, and antigens that distinguish cells belonging to distinct differentiation lineages or distinguish cells at different phases in the same differentiation lineage may be observed if the correct antibody is available. Initial recognition of differentiation antigens came about through analysis of surface antigens of T-cell leukemias of the mouse and the description of the TL, Thy-1, and Lyt series of antigens. The analysis of these T-cell differentiation antigens was greatly simplified by the availability of normal T cells and B cells of mouse and man and is relatively advanced, but little is known about differentiation antigens displayed on normal and neoplastic cells belonging to other lineages. This is due to the difficulty of obtaining a ready source of the appropriate normal cell type.

Progress in defining surface antigens on melanocytes was made possible by the recently discovered technique of culturing melanocytes from normal skin (Eisinger, M. et al. Proc. Natl. Acad. Sci. U.S.A. 79:2018 (1982)). This method provides a renewable source of proliferating cells for the analysis of melanocyte differentiation antigens. Likewise, a large number of cell lines derived from melanomas have now been established and these have facilitated the analysis of melanoma surface antigens. The advent of MAB has greatly accelerated knowledge about the surface antigens of malignant melanoma Kaprowski, H. et al. Proc. Natl. Acad. Sci. U.S.A. 75:3405 (1978): Yeh, M-Y., Proc. Natl. Acad. Sci. U.S.A. 76:2927 (1979): Dippald, W. G. et al. Proc. Natl. Acad. Sci. U.S.A. 77:6114 (1980): Carrel, S., et al. Cancer Res. 40:2523 (1980).

By means of the monoclonal antibodies of the present invention, cell markers on both melanomas and melanocytes have been identified. A panel of typing monoclonal antibodies has been selected which recognizes differentiation antigen characteristics at each stage of development in both melanocytes and melanomas. These differentiation antigens may be used to classify melanocytes and melanomas and to group them into characteristic sub-sets.

Immunoassay of melanocytes and melanoma cells within sub-sets is thus made possible.

SUMMARY OF THE INVENTION

The monoclonal antibodies of the present invention were prepared by the Kohler-Millstein procedure wherein spleen cells from a mouse immunized with a cultured melanocyte glioma, renal cancer or melanoma cell were fused with a myloma cell to form hybridomas. Antibodies from these hybridomas were discovered which recognize differentiation antigens on melanocytes and melanoma cells at various stages of maturity. A system of classification of melanocytes and melanomas based on these differentiation antigens is proposed and serological assays for melanocytes and melanomas at various stages of differentiation using monoclonal antibodies to these markers have been developed. These assays are of special use in the early diagnosis of melanoma.

The assay of the present invention comprises contacting a tissue containing melanoma cell with the antibody recognizing melanoma cell antigens, preferably monoclonal antibodies to one or more cell antigens of the antigenic system $M_1$ through $M_{34}$ and observing the antigenic reaction between said monoclonal antibody and said antigen. In a preferred embodiment of the invention the tissue contacted is a blood sample and the antigenic reaction is observed by radioimmunoassay or enzyme-linked immunoassay. In another embodiment of the present invention the tissue to be assayed is first excised and is then either freshly or after being frozen or embedded in paraffin by methods well-known in the art contacted with said monoclonal antibodies. In this embodiment said antibodies may be tagged with colored groups or color forming substances such as enzymes, preferably peroxidase and its substrates, with flourescent substances or with radioactive elements by which the location of the antibodies may be traced. Serological assay of excised tissue is also an embodiment of the present invention. Thus passive hemmaglutination, antibody inhibition assay, or glycolipid-mediated immune adherence assay may be used. Likewise anti-mouse immunoglobulin assay and Protein A assays may be employed.

In another preferred embodiment of the present invention, the tissue to be assayed comprises the intact body of an individual or a whole portion thereof, the antibody is administered to the individual, the antibody having been tagged with a radioactive or other energy-producing element, and the whole body or part thereof is scanned externally for localization of radioactivity at the site of melanoma cells.

The method of the present invention also comprises treatment of melanomas in a patient wherein the monoclonal antibody recognizing the cell antigen of melanoma cells, preferably the cell differentiation antigen, is administered to the patient in an amount effective to inhibit the growth or proliferation of melanoma cells. In a preferred embodiment of this method the antibody is tagged with a potentially tissue destructive agent which causes destruction of the melanoma cells. Examples of tissue destructive agents comprise chemotoxic agents, chemotherapeutic agents, radionucleides, toxins, complement activators and clotting activators.

The method of the present invention also comprises a method of treating disorders of the pigment cells in an individual comprising administering to said individual monoclonal antibodies recognizing cell antigens of melanocytes. Nevi, for example, is one such pigment disorder which may be so treated.

DETAILED DESCRIPTION OF THE INVENTION

Description of antibodies in typing panel and antigens recognized

The following description is intended to illustrate this invention without limiting same in any manner especially with respect to substantially functional equivalents of hybridomas, monoclonal antibodies and cell lines described and claimed herein.

The monoclonal antibodies selected for use in the present invention were derived from spleen cells of mice immunized with melanoma, glioma, renal cancer or melanocyte cell cultures by fusion methods well known in the art (ref. Kohler). A group of Monoclonal antibodies hereinafter termed "panel" was selected which were found to recognize specific cell surface antigens on melanocytes. This panel and the antigenic systems recognized are given in Table 1. Monoclonal antibodies designated $R_{24}$, $I_{12}$, $L_{10}$, $K_5$, $I_{24}$ and $R_8$ were reported by Dippold et al. (Proc. Nat'l. Acad. Sci. U.S.A., 77, 6114 (1980)) (Co-pending U.S. patent application No. 307,060), monoclonal antibodies designated $V_2$ and $S_6$ were reported by Ueda et al., (Prod. Nat'l. Acad. Sci. U.S.A. 78, 5122 (1981)). (Co-pending U.S. patent application No. 413,861) and antibody Mel-1 was reported by Houghton et al., (Prod. Nat'l. Acad. Sci. U.S.A., 77, 4260 (1980)).

The following hybridomas were deposited with the American Type Culture Collection (ATCC), Rockville, Md., U.S.A. 20852 on Nov. 30, 1983 and allotted the following ATCC accession numbers:

| Hybridoma | ATCC Accession Number |
|---|---|
| Hybridoma M-1 (L 127) | HB 8437 |
| Hybridoma M-4 (M 111) | HB 8438 |
| Hybridoma M-8 (D14) | HB 8439 |
| Hybridoma M-10 (M 144) | HB 8440 |
| Hybridoma M-11 (A 127) | HB 8441 |
| Hybridoma M-12 (L 166) | HB 8442 |
| Hybridoma M-13 (E 20) | HB 8443 |
| Hybridoma M-16 (K 114) | HB 8444 |
| Hybridoma M-18 (R 24) | HB 8445 |
| Hybridoma M-19 (L 235) | HB 8446 |
| Hybridoma M-20 (L 101) | HB 8447 |
| Hybridoma M-23 (L 230) | HB 8448 |
| Hybridoma M-24 (M 138) | HB 8449 |
| Hybridoma M-25 (M 368) | HB 8450 |
| Hybridoma M-26 (A 123) | HB 8451 |
| Hybridoma M-27 (A 124) | HB 8452 |
| Hybridoma M-28 (B 5) | HB 8453 |

These deposits were made pursuant to the provisions of the Budapest Treaty on the International Recognition of the Deposit of Microorganisms For the Purposes of Patent Procedure.

TABLE I

| | PANEL OF MOUSE MONOCLONAL ANTIBODIES DETECTING CELL SURFACE ANTIGENS OF MELANOMAS AND MELANOCYTES** | | |
|---|---|---|---|
| Cell Surface Antigen System | Deposit Number of Monoclonal Antibody | Immunizing Cell Type and Number | Reference |
| M-1 | L1-27 | Melanoma SK-MEL-33 | |
| M-2 | A010 | Glioma AO | 10 |
| M-3 | A092 | Glioma AO | 10 |
| M-4 | M111 | Cutaneous melanocytes | |
| M-5 | M231 | Cutaneous melanocytes | |
| M-6 | AJ8 | Glioma AJ | 10 |
| M-7 | AJ117 | Glioma AJ | 10 |
| M-8 | D14 | Melanoma DX-2 | |
| M-9 | Mel-1* | | 12 |
| M-10 | M144 | Cutaneous melanocytes | |
| M-11 | A1-27 | Melanoma SK-MEL-19 | |
| M-12 | L166 | Melanoma SK-MEL-33 | |
| M-13 | E20 | Melanoma SK-MEL-93 | |
| M-14 | AJ225 | Glioma AJ | 10 |
| M-15 | AJ9 | Glioma AJ | 10 |
| M-16 | K1114 | Melanoma SK-MEL-31 | |
| M-17 | AJ60 | Glioma AJ | 10 |
| M-18 | $R_{24}$ | Melanoma SK-MEL-28 | 3 |
| M-19 | $I12,L_{10},K_5,L235$ | Melanoma SK-MEL-28,33 | 3 |
| M-20 | L101,Q$_{24}$,Q$_{14}$,829, 846 | Melanoma SK-MEL-28,33,93, | |
| M-21 | $I_{24}$ | Melanoma SK-MEL-28 | 3 |
| M-22 | $R_8$ | Melanoma SK-MEL-28 | 3 |
| M-23 | L2-30,L254 | Melanoma SM-MEL-33 | |
| M-24 | M138 | Cutaneous melanocytes | |
| M-25 | M3-68 | Cutaneous melanocytes | |
| M-26 | A123 | Melanoma SK-MEL-19 | |
| M-27 | A124 | Melanoma SK-MEL-19 | |

TABLE I-continued
PANEL OF MOUSE MONOCLONAL ANTIBODIES DETECTING CELL SURFACE ANTIGENS OF MELANOMAS AND MELANOCYTES**

| Cell Surface Antigen System | Deposit Number of Monoclonal Antibody | Immunizing Cell Type and Number | Reference |
|---|---|---|---|
| M-28 | B5 | Melanoma SM-MEL-93 | |
| M-29 | AJ2 | Glioma AJ | 10 |
| M-30 | AJ10 | Glioma AJ | 10 |
| M-31 | A050 | Glioma AO | 10 |
| M-32 | A0122 | Glioma AO | 10 |
| M-33 | $V_2$ | Renal cancer SK-RC-6 | 9 |
| M-34 | $S_6$ | Renal cancer SK-RC-7 | 9 |

*Defined by naturally occuring antibody in human serum that defines the Mel-1 melanocyte differentiation antigen.
**The antibodies, hybridomas and cell lines identified in Table 1 bear the designated deposit number and are deposited with Sloan-Kettering Institute, 1275 York Avenue, New York, New York 10021.

In the table above, the numbers in the Reference column identify the following literature publications:

Reference number 3 is Dippald, et al. Proc. Nat'l. Acad. Sci. U.S.A. 77:6114 (1980); reference number 10 is Cairncross, et al., Proc. Nat'l. Acad. Sci. U.S.A. (1981); reference number 9 is Ueda, et al., Proc. Nat'l. Acad. Sci. U.S.A. 78:5122 (1981); and reference number 12 is Houghton, et al. Proc. Nat'l. Acad. Sci. U.S.A. 77:4260 (1980).

Melanocyte Differentiation Antigens

Melanocyte antigens (markers) detected by this panel of typing antibodies can be grouped into four categories: (1) not detected on newborn or adult melanocytes but expressed by subsets of melanoma: HLA-DR, M-1, and M-3; (2) detected on newborn melanocytes but not adult melanocytes; M-4 to M-8; (3) detected on adult melanocytes and only weakly, or not at all, on most newborn melanocytes: M-9 and M-10; and (4) detected equally on both newborn and adult melanocytes: M-11 to M-34. As Table 1 shows, monoclonal antibodies known to identify the same epitope or different epitopes on the same molecule were grouped under the same antigenic system; M-19 antigen is a 95 kd glycoprotein detected by four mouse monoclonal antibodies, M-20 represents a 130 kd glycoprotein detected by five different mouse monoclonal antibodies, and M-23 is a glycoprotein dimer of 145 kd and 100 dk detected by two antibodies.

FIG. 1 illustrates the serological typing of newborn and adult melanocytes for cell surface antigens.

Serological typing was by anti-mouse immunoglobulin (anti-Ig) assay and Protein A (AP) assays by methods known in the art as, for example, those described by Dippold (Dippold, W. G. et al., supra (1980)) and Pfreundschuh, M. et al., (Proc. Nat'l. Acad. Sci., U.S.A., 75, 5122 (1980)). In preferred procedures, indicator cells are prepared by conjugating purified antimouse immunoglobulin or Protein A to human erythocytes using 0.01% chromium chloride. Assays were performed in Falcon 3040 Microtest II plates. Sera was incubated with target cells for 1 hour. Plates were washed and evaluted for rosetting by light microscopy. Titers corresponded to the serum dilution giving 50% positive target cells. Absorption tests were carried out by the methods of Kippold (supra) and Pfreundschuh (supra).

Sera from tumor-bearing mice, nu nu mice (Swiss background) innoculated with cloned hybridomas, were used for serological analysis. These sera had maximum filters of $\geq 10^{-4}$ and usually $\geq 10^{-5}$ with melanoma or melanocyte cultures. Mouse monoclonal antibody and conventional rabbit antisera to b2-microglobulin (018b) were purchased from Accurate Chemical and Scientific Corp., Hicksville, N.Y.

Twenty-four other monoclonal antibodies detecting a series of differentiation antigens on renal cancer, lung cancer, and ovarian cancer and ABH blood group antigens were included in these selection tests. No reactions with newborn or adult melanocytes were observed with these MAb so they were excluded from the panel.

Subsets of Melanoma Cell Lines Defined by Melanocyte Differentiation Antigen The panel of typing antibodies given in Table 1 was used to identify melanoma surface antigens. Table 2 shows the reactivity and titer of each member of the panel with cultured melanoma cell lines.

TABLE 2
SEROLOGICAL TYPING OF MELANOMA CELL LINES BY MOUSE MONOCLONAL ANTIBODIES

| Cell Surface Antigen System | Melanoma Cell Lines Reactive/Tested (Titer Range) |
|---|---|
| HLA-A,B,C, | 9/11 ($10^{-5}$–$10^{-6}$) |
| B$_2$-microgloubulin | 37/38* |
| HLA-DR | 13/21 ($10^{-3}$–$10^{-5}$) |
| M-1 | 5/32 ($10^{-4}$–$10^{-5}$) |
| M-2 | 6/28 ($10^{-3}$–$10^{-5}$) |
| M-3 | 17/31 ($10^{-3}$–$10^{-4}$) |
| M-4 | 16/33 ($10^{-4}$–$10^{-7}$) |
| M-5 | 10/23 ($10^{-3}$–$10^{-5}$) |
| M-6 | 12/31 ($10^{-3}$–$10^{-5}$) |
| M-7 | 10/10 ($10^{-4}$–$10^{-5}$) |
| M-8 | 17/18 ($10^{-4}$–$10^{-5}$) |
| M-9 | 22/43 ($10^{-2}$–$10^{-5}$) |
| M-10 | 5/33 ($10^{-3}$–$10^{-4}$) |
| M-11 | 19/33 ($10^{-4}$–$10^{-6}$) |
| M-12 | 16/19 ($10^{-4}$–$10^{-6}$) |
| M-13 | 15/15 ($10^{-5}$–$10^{-6}$) |
| M-14 | 3/13 ($10^{-3}$–$10^{-5}$) |
| M-15 | 10/10 ($10^{-4}$–$10^{-5}$) |
| M-16 | 10/34 ($10^{-3}$–$10^{-5}$) |
| M-17 | 16/16 ($10^{-3}$–$10^{-5}$) |
| M-18 | 16/16 ($10^{-3}$–$10^{-5}$) |
| M-19 | 20/29 ($10^{-4}$–$10^{-6}$) |
| M-20 | 24/27 ($10^{-5}$–$10^{-6}$) |
| M-21 | 16/16 ($10^{-3}$–$10^{-5}$) |
| M-22 | 9/16 ($10^{-4}$–$10^{-6}$) |
| M-23 | 19/19 ($10^{-5}$–$10^{-7}$) |
| M-24 | 22/26 ($10^{-5}$–$10^{-7}$) |
| M-25 | 23/26 ($10^{-5}$–$10^{-6}$) |
| M-26 | 17/19 ($10^{-4}$–$10^{-7}$) |
| M-27 | 14/33 ($10^{-3}$–$10^{-6}$) |
| M-28 | 9/10 ($10^{-4}$–$10^{-5}$) |
| M-29 | 10/10 ($10^{-5}$–$10^{-6}$) |
| M-30 | 9/10 ($10^{-5}$–$10^{-6}$) |
| M-31 | 8/10 ($10^{-4}$–$10^{-6}$) |

TABLE 2-continued
SEROLOGICAL TYPING OF MELANOMA CELL LINES BY MOUSE MONOCLONAL ANTIBODIES

| Cell Surface Antigen System | Melanoma Cell Lines Reactive/Tested (Titer Range) |
|---|---|
| M-32 | 8/10 ($10^{-4}$–$10^{-6}$) |
| M-33 | 6/6 ($10^{-5}$–$10^{-6}$) |
| M-34 | 2/30 ($10^{-3}$–$10^{-4}$) |

*Determined by absorption tests; rabbit antihuman $B_2$-microgloubulin (diluted according to endpoint) was absorbed with individual melanoma cell lines and residual antibody activity tested against a standard melanoma target cell line (SK-MEL-28).

It was found that the typing antibodies listed in Table 1 generally react with only a proportion of the melanoma cell lines, and therefore divide melanomas into distinguishable subsets on the basis of antigenic phenotypes. Antigens such as M-25 are expressed by most melanoma lines (23/26 lines), antigens M-4 and M-6 are detected on approximately one-half of the cell lines, and M-10 antigen is found on only 5 of 33 melanoma lines. With regard to MHC products, HLA-DR expression was found on 13 of 21 cell lines. Antibodies to HLA-A,B,C and b2-microglobulin were highly reactive with nearly all melanoma cell lines; two lines, SK-MEL-19 and SK-MEL-33, showed no reaction. By absorption tests, these antigens were detectable on SK-MEl-19 but not on Sk-MEl-33.

The markers thus identified provide new ways to analyze and classify melanoma. For instance, melanoma cell lines fall into one of three general classes on the basis of expression of early, intermediate or late melanocyte differentiation antigens. There is an evident correlation between the surface antigenic phenotype of the cultured melanoma line and other differentiation characteristics, such as morphology, pigmentation and tyrosinase activity. Melanomas expressing early markers but lacking intermediate or late markers have an epitheliai morphology, lack pigmentation, and have low levels of tyrosinase. In contrast, melanomas expressing late markers, such as M-9 and M-10, have a spindle-shaped or polydenritic morphology, are pigmented, and have high levels of tyrosinase. Intermediate classes of melanoma can be distinguished that express intermediate melanocyte markers, and these generally have a spindle morphology, little pigmentation and low levels of tyrosinase.

Tyrosinase activity was measured using a modification of the assay described by Pomerantz (Pomerantz, S. H., J. Biol. Chem. 241, 161 (1966). [$^3$H]tyrosine (specific activity 53.1 Ci/mMol) was purchased from New England Nuclear. Cell lines to be tested were seeded at a density of $1 \times 10^6$ cells per flask in 25 cm$^2$ Falcon flasks. After 12 hours, medium was removed and replaced with 4 ml. fresh medium containing 5 uCi [$^3$H]tyrosine in the medium was removed by adsorption to activated charcoal and passage over a Dowex 50w column. Tritiated $H_2O$ (generated by tyrosinase activity) in the eluent was counted in triplicate in LS 9000 Beckman Scintillation Counter. Tyrosinase activity was expressed as the ratio of tritiated $H_2O$ generated by melanoma cell lines/tritiated $H_2O$ generated by control nonpigmented renal cancer cell line (SK-RC-7).

Twenty-five melanoma cell lines were typed for the expression of M-2, M-3, HLA-DR, M-4, M-6, M-9 and M-10 antigens. These seven antigens were selected because they defined subsets of melanomas, being present on some melanomas but not others, and had distinct patterns of expression of fetal/newborn and adult melanocytes. Three antigens, HLA-DR, M-2, and M-3, can be assumed to be early markers of melanocytes. Antigens M-4 and M-6 appear on fetal and newborn melanocytes, but not adult melanocytes, and therefore signal an intermediate phase in melanocyte differentiation. M-9 and M-10 appear to be late markers in the melanocyte lineage, because they are strongly expressed on adult melanocytes as compared to fetal and newborn melanocytes. FIG. 2 illustrates serological typing of melancytes and melanoma cells for these HLA-DR, M-4 and M-10 cell surface antigens by anti-Ig assay.

In summary, the surface phenotypes of the twenty-five melanoma lines appear to correspond to early, intermediate, or late phases of melanocyte differentiations. Five melanomas expressed only early markers, ten intermediate markers and ten late melanocyte (FIG. 2). Evidence for the significance of these differences comes from a comparison of the pattern of surface antigens with other differentiation characteristics, such as pigmentation, morphology, and tyrosinase. The majority of melanomas expressing early antigenic markers are epithelioid and these melanoma lines lack pigmentation and tyrosinase activity. Melanomas expressing late melanocyte markers frequently have a polydendritic morphology, similar to adult melanocytes, with heavy pigmentation and high levels of tyrosinase activity.

| MELANOMA CELL SURFACE ANTIGEN | FIG. 1 | |
|---|---|---|
| | NEWBORN MELANOCYTES | ADULT MELANOCYTES |
| HLA-DR | ○○○○○○○○○○ | ○○○○○○○○○ |
| M-1 | ●●○○○○○○○○ | ○○○○○○○○ |
| M-2 | ○○○○○○ | ○○○○○ |
| M-3 | ○○○○○○○ | ○○○○○○ |
| M-4 | ●●●●●●○○ | ○○○○○○ |
| M-5 | ●●●●●○○ | ○○○○○ |
| M-6 | ●●●●●●○ | ○○○○ |
| M-7 | ●●●○○ | ○○○ |
| M-8 | ●●○○○ | ○○○○○ |
| M-9 | ●○○○○○○○○○ | ●●●●●●●● |
| M-10 | ●●○○○○○○○ | ●●●●●● |
| M-11 | ●●○○○○ | ●●○○○ |
| M-12 | ●●○○○ | ●●○○○ |
| M-13 | ●●●●○ | ●○○ |
| M-14 | ○○○○ | ○○ |
| M-15 | ●●●○ | ●○○ |
| M-16 | ●○○○○○ | ○○○○○○ |
| M-17 | ●○○○ | ○○○ |
| M-18 | ●●●●●●○○ | ●●●●●○ |
| M-19 | ●●●●●●●●● | ●●●●●●●●○ |
| M-20 | ●●●●●●● | ●●●●● |
| M-21 | ●●● | ● |
| M-22 | ●● | ● |
| M-23 | ●●● | ●●●● |
| M-24 | ●●●●○ | ●●●● |
| M-25 | ●●●●● | ●●●● |
| M-26 | ●●●●●● | ●●●● |
| M-27 | ●●●●●●● | ●●●● |
| M-28 | ●●●○ | ●●● |
| M-29 | ●●● | ●● |
| M-30 | ●●● | ●● |
| M-31 | ●●● | ●● |
| M-32 | ●●● | ●● |
| M-33 | ●●● | ●●● |
| M-34 | ●●●●●●●● | ●●●●● |
| HLA-A,B,C | ●●●●● | ●●●● |
| B$_2$m | ●●● | ●● |

Serological typing of newborn and adult melanocytes for melanoma cell surface antigens. Each circle represents an individual test, and each test for a particular antigen was performed with melanocytes from a different individual. In the case of tests with mouse monoclonal antibodies, black circles represent antibody titers 1:10$^4$ to 1:10$^7$, stippled circles 1:500 to 1:5000, and open circles 1:250. In tests with human typing serum detecting M-14 antigen, black circles represent titers 1:500 to 1:10$^4$, stippled circles are 1:10 to 1:250, and open circles are unreactive (1:10).

visually by the intensity of brown or black pigment in the cell pellet. Tyrosinase activity was expressed as a ratio of tritiated H$_2$O produced by melanoma culture/nonpigmented renal cancer culture (standard).

What is claimed is:

1. A hybridoma cell line which produces a monoclonal antibody capable of specifically binding to melanocytes, the cell line being selected from the group consisting of hybridoma M-4 (ATCC No. HB 8438) and hybridoma M-10 (ATCC No. HB 8440).

2. A monoclonal antibody produced by hybridoma cell line of claim 1.

3. A monoclonal antibody of claim 2 tagged with a color-forming fluorescent or radioactive substance.

FIG. 2

| Melanoma Cell Line | Melanoma Cell Surface Antigen | | | | | | | Morphology | Pigmentation | Tyrosinase Activity |
|---|---|---|---|---|---|---|---|---|---|---|
| | M-2 | M-3 | HLA-DR | M-4 | M-6 | M-9 | M-10 | | | |
| KK-MEL-31 | ■ | ■ | | | | | | E | — | 1.0 |
| SK-MEL-37 | ■ | ■ | | | | | | E | — | 1.1 |
| SK-MEL-172 | | ■ | ■ | | | | | E | — | 1.0 |
| SK-MEL-63 | | ■ | | | | | | E | — | 1.3 |
| SK-MEL-170 | | | ■ | | | | | E-S | — | 1.0 |
| SK-MEL-65 | ■ | | ■ | | | | | E | — | 1.2 |
| SK-MEL-173 | | ■ | ■ | ■ | | | | E-S | — | 1.3 |
| SK-MEL-166 | | ■ | ■ | | | | | E-S | — | 1.2 |
| SK-MEL-131 | | ■ | ■ | | | | | S | — | 1.2 |
| SK-MEL-118 | ■ | ■ | ■ | ■ | | | | E-S | — | 1.0 |
| SK-MEL-13 | | ■ | ■ | | | | | S | + or − | 1.9 |
| SK-MEL-163 | | | ■ | ■ | | | | S | — | 1.0 |
| SK-MEL-96 | | | ■ | ■ | | | | S | + or − | 1.1 |
| SK-MEL-30 | | | ■ | | | | | S | + + | 5.5 |
| SK-MEL-93 | | ■ | | ■ | ■ | | | S | + or − | 1.3 |
| SK-MEL-165 | | ■ | ■ | ■ | | | | S | + or − | 1.3 |
| SK-MEL-28 | | ■ | ■ | ■ | ■ | | | S | + or − | 1.4 |
| SK-MEL-75 | | ■ | ■ | ■ | ■ | | | S | + or − | 1.4 |
| MeWo | | ■ | | ■ | ■ | | | S | +0 or − | 1.5 |
| SK-MEL-127 | | | ■ | ■ | ■ | | | S-D | + + | 4.1 |
| SK-MEL-29 | | | ■ | | ■ | ■ | | S | + or − | 1.6 |
| SK-MEL-64 | | | | | ■ | ■ | | S | + + | 3.0 |
| SK-MEL-23 | | | | ■ | ■ | ■ | | S | + + + | 3.3 |
| SK-MEL-19 | | | | ■ | ■ | ■ | ■ | S-D | + + | 7.8 |
| SK-MEL-110 | | | | | | ■ | ■ | S-D | + or − | 1.8 |

Serological typing of 25 melanoma cell lines for melanocyte differentiation markers. Black rectangles represent antigen expression by melanoma cell lines, as determined by titers of 1:500 to 1:10$^7$ for mouse monoclonal antibodies and 1:10 to 1:10$^5$ for human serum detecting M-10 antigen. Morphology: E, epithelioid; S, spindle-shaped; D, polydendritic. Pigmentation was estimated